(12) United States Patent
Kurek et al.

(10) Patent No.: US 8,110,113 B2
(45) Date of Patent: Feb. 7, 2012

(54) HIGH-THROUGHPUT EVALUATION OF RUBISCO AND PLANT PHOTOSYNTHETIC PERFORMANCE IN VIVO

(75) Inventors: Itzhak Kurek, San Francisco, CA (US); Xuehua Hu, Foster City, CA (US); Genhai Zhu, San Jose, CA (US); Lu Liu, Palo Alto, CA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 722 days.

(21) Appl. No.: 12/110,776

(22) Filed: Apr. 28, 2008

(65) Prior Publication Data

US 2008/0271209 A1      Oct. 30, 2008

Related U.S. Application Data

(60) Provisional application No. 60/914,960, filed on Apr. 30, 2007.

(51) Int. Cl.
*B01D 15/36*     (2006.01)

(52) U.S. Cl. ........... 210/659; 436/63; 436/161; 436/173

(58) Field of Classification Search ................... 210/259; 436/63, 161, 173
See application file for complete search history.

(56) References Cited

OTHER PUBLICATIONS

Jakob, R., et al. FEBS; Apr. 1985, vol. 183, No. 1; pp. 111-114.*
Luo, B. et al. Journal of Chromatography A (2007); vol. 1147; pp. 153-164 available online Feb. 16, 2007.*
Cen, Yan-Ping et al., "The Regulation of Rubisco Activity in Response to Variation in Temperature and Atmospheric CO2 Partial Pressure in Sweet Potato", Plant Physiology, Oct. 2005, vol. 139, pp. 979-990.
He, Zhili et al., "Ribulose-1,5-Bisphosphate Carboxylase/Oxygenase Activase Deficiency Delays Senescence of Ribulose-1,5-Bisphosphate Carboxylase/Oxygenase but Progressively Impairs Its Catalysis during Tobacco Leaf Development", Plant Physiology, (1997) vol. 115: pp. 1569-1580.
Whitney, Spencer M. et al., "Photosynthesis and Growth of Tobacco with a Substituted Bacterial Rubisco Mirror the Properties of the Introduced Enzyme", Plant Physiology, Sep. 2003, vol. 133, pp. 287-294.

* cited by examiner

*Primary Examiner* — Russell Kallis
(74) *Attorney, Agent, or Firm* — Alston & Bird LLP

(57) ABSTRACT

The present invention provides a method for determining a level of a RuBP, PGA, 2-PA in a photosynthetic cellular extract by resolving at least one RuBP, PGA, or 2-PA or combinations thereof in a photosynthetic cellular extract obtained from a plant. In another aspect, it provides for detecting at least one resolved RuBP, PGA, or 2-PA or combinations, thereby determining a level of the resolved RuBP, PGA, or 2-PA or combinations. In one aspect the photosynthetic cellular extract is obtained from a plant subjected to an abiotic stress. A method of the invention can be useful, for example, for identifying plants with increased photosynthetic performance. Also included herein is a high throughput system for identifying a plant with increased photosynthetic performance.

38 Claims, 11 Drawing Sheets

HIGH-THROUGHPUT EVALUATION OF RUBISCO AND PLANT PHOTOSYNTHETIC PERFORMANCE IN VIVO

CROSS-REFERENCE TO RELATED APPLICATIONS

This application claims priority under 35 U.S.C. §119 of a provisional application Ser. No. 60/914,960 filed Apr. 30, 2007, which application is hereby incorporated by reference in its entirety.

BACKGROUND OF THE INVENTION

Growth and biomass accumulation of a plant is dependent on photosynthetic $CO_2$ assimilation. Ribulose-1,5-bisphosphate (RuBP) carboxylase/oxygenase (Rubisco) is the first enzyme involved in the conversion of $CO_2$ into carbohydrates and its activity often limits plant photosynthetic rate. Many environmental changes, such as light intensity, temperature and drought can influence photosynthesis by affecting Rubisco performance.

Detection of RuBP and 3-phosphoglycerate (PGA) has been previously described by Whitney, S. M and Andrews, T. J (Plant Physiol. 2003, 133:287-294) and Cen, Y-P and Sage, R. F. (Plant Physiol. 2005, 139:979-990). In both publications the quantification of RuBP was coupled with Rubisco carboxylation of RuBP with $^{14}C$ detection or NADH oxidation at 340 nm in a downstream reaction. PGA was assayed in coupled enzymatic assay and monitored at 340 nm for oxidation of NADH. Chakrabarti, S et al (J. Biochem. Biophys Methods, 2002 52:179-187) reported a detection and quantitation method for both RuBP and PGA based on a thin-layer chromatographic method. The major limitations of the current assays are low sensitivity and low throughput. There are no published methods that describe the direct, simultaneous detection and quantification of 2-phosphoglycolate (2-PA) with RuBP and PGA in planta.

For these and other reasons, there exists a need for the present invention.

BRIEF SUMMARY OF THE INVENTION

The present invention provides methods for resolving and measuring RuBP, PGA or 2-PA or combinations of RuBP, PGA, or 2-PA in a photosynthetic cellular extract. In one aspect, the method includes introducing a photosynthetic cellular extract from a plant into a reverse phase chromatography column. Reverse phase high performance liquid chromatography is performed on the extract to detect and measure the levels of RuBP, PGA, or 2-A or combinations of RuBP, PGA, or 2-A.

The methods of the invention are useful in identifying a plant with increased photosynthetic performance. In one aspect, the method includes introducing a photosynthetic cellular extract from a first plant and a second plant respectively into a reverse phase chromatography column. In the methods of the invention, reverse phase high performance liquid chromatography is performed on the extract to detect and measure the levels of RuBP, PGA, or 2-A or combinations of RuBP, PGA, or 2-A. The resolved RuBP, 2-A or PGA, or combinations of RuBP, 2-A or PGA are detected and measured using tandem mass spectrometry. In one aspect, a level of PGA and a ratio of PGA/RuBP in the cellular extract from each plant are determined.

In another aspect, a level of 2-A and a ratio of 2-PA/PGA in the cellular extract from each plant are determined.

In another aspect, the level of PGA and the ratio of PGA/RuBP of the first plant are compared to the level of PGA and the ratio of PGA/RuBP from the second plant. A plant that has a level of PGA and a PGA/RuBP ratio that are greater than the level of PGA and the PGA/RuBP ratio from the second plant is indicative of a plant with increased photosynthetic performance.

In another aspect, the level of 2-A and the ratio of 2-PA/PGA of the first plant are compared to the level of 2-A and the ratio of 2-PA/PGA from the second plant. The plant that has a level of 2-A and a 2-A/PGA ratio that are less than the level of 2-A and the ratio of 2-PA/PGA from the other plant is indicative of a plant with increased photosynthetic performance.

The present invention also provides for a high throughput system for identifying a plant with increased photosynthetic performance. The system includes introducing into a multi-well plate a photosynthetic cellular extract from at least one plant. The photosynthetic cellular extract is introduced into a reverse phase chromatography column via an automated solid phase extraction system. Reverse phase high performance liquid chromatography is performed on the extract to generate HPLC eluates comprising RuBP, PGA, or 2-A or combinations of RuBP, PGA, or 2-A. The eluates are introduced into a mass spectrometer and the levels of the RuBP, PGA, or 2-A or combinations of RuBP, PGA, or 2-A are detected and measured with tandem (MS/MS) mass spectrometry.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE PREFERRED EMBODIMENT

Figure 1:
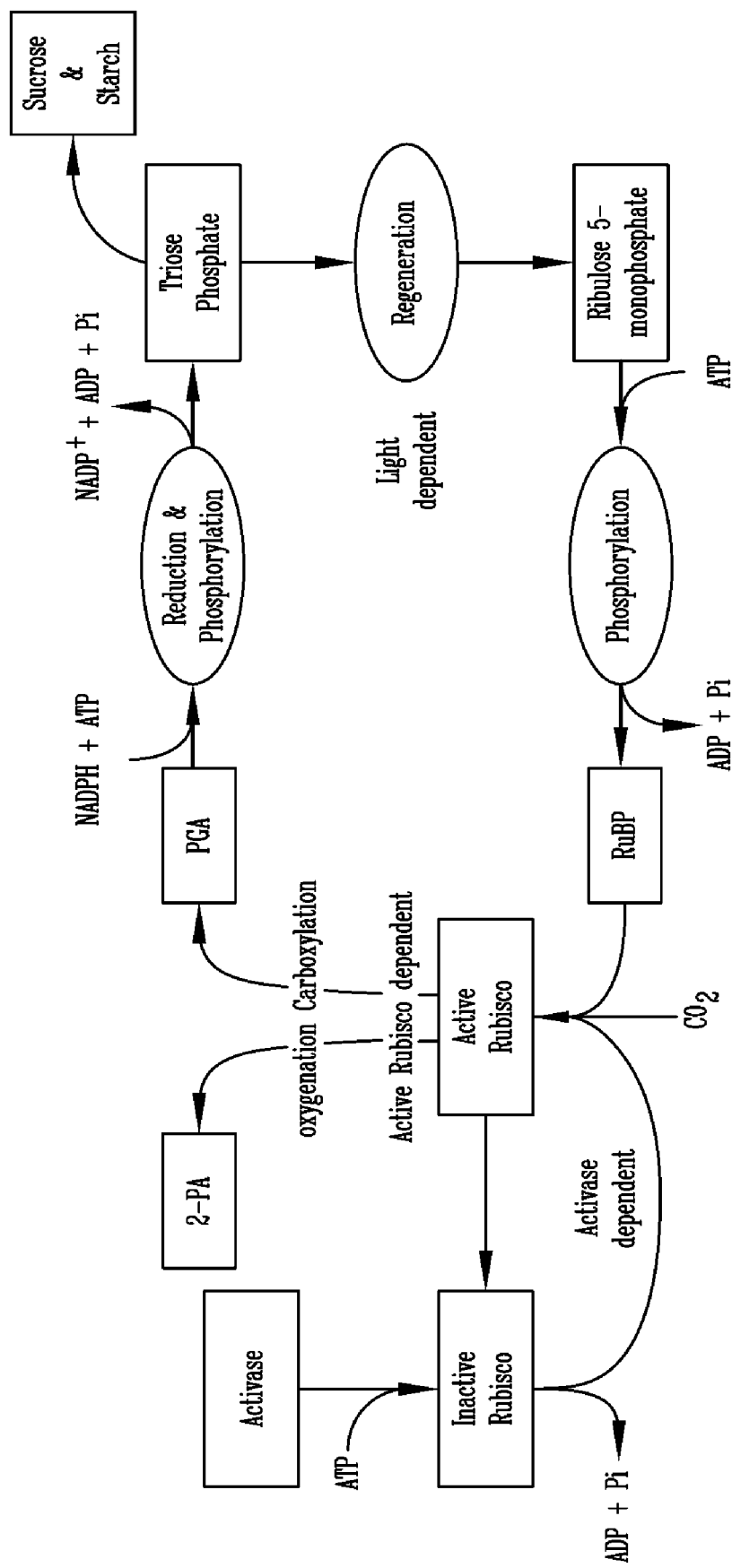
FIG. 1. Schematic presentation of Rubisco activity and regulation.
Figure 2A:
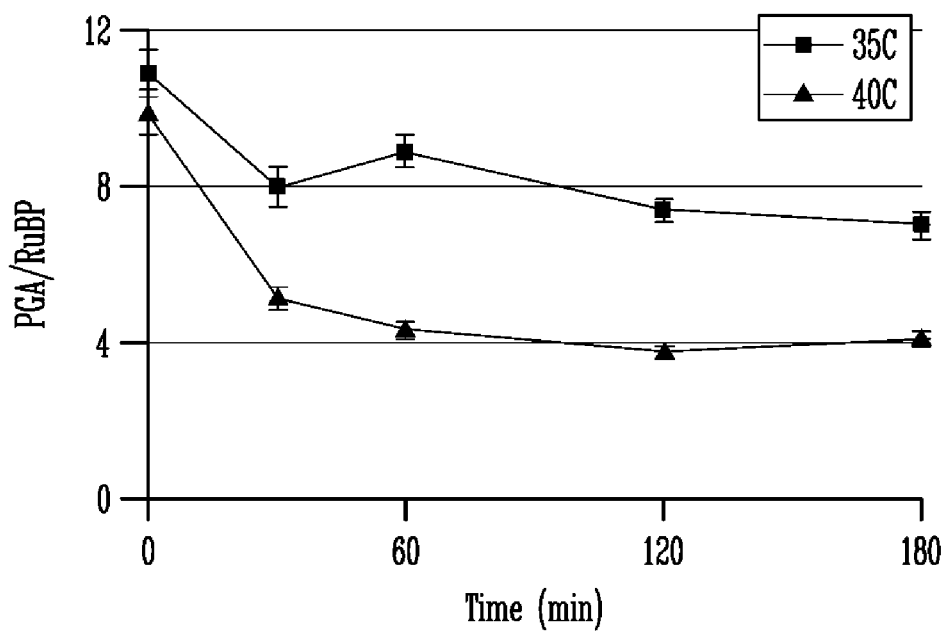
FIG. 2. The effect of heat stress on PGA/RuBP (A) and PGA (B) in maize plants grown at 27° C. exposed to different heat treatment. Plants grown at 27° C. under 400 μmol photons $m^{-2} s^{-1}$ light intensity and 40% humidity were sampled and transferred to growth chamber for heat treatment at 35° C. or 40° C. under the same light intensity and humidity described above. At the indicated times, 3 samples (each represent 3 independent plants) were collected and analyzed for PGA and RuBP levels. Heat stress directly reduces the activity of the thermo-labile RCA (Rubisco activase). As a result, Rubisco Carboxylation activity was inhibited (lower PGA/RuBP). Exposure to 40° C. leads to a significant decrease.
Figure 2B:
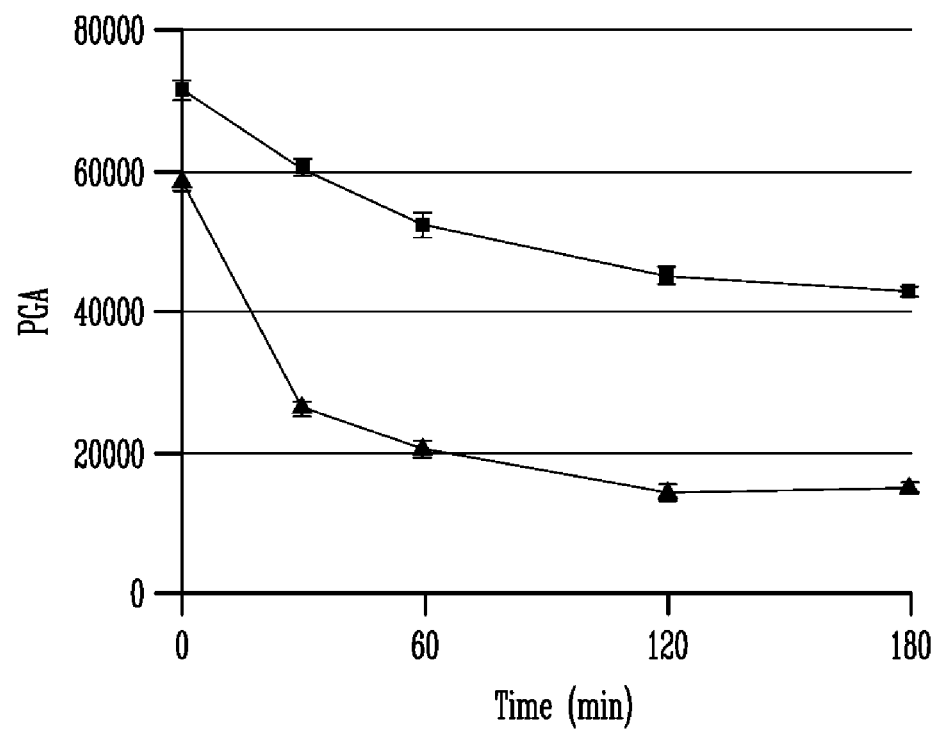
Figure 3:
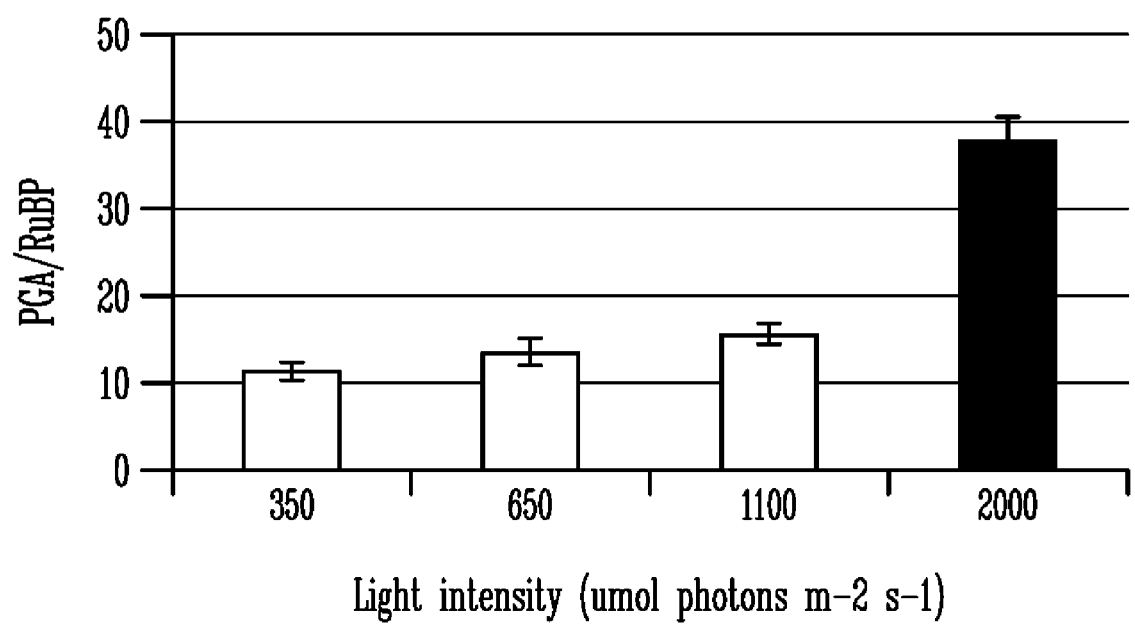
FIG. 3. The effect of light intensity on PGA/RuBP in maize plants grown at 27° C. and 40% humidity. Plants were grown at the indicated light intensities for 2 hours under the temperature and humidity described above. At the end of the light treatment 3 samples (each represent 3 independent plants) were collected and analyzed for PGA and RuBP levels. Under low light conditions (350-1100 μmol photons $m^2 S^{-1}$) photosynthesis is inhibited by RuBP regeneration and PGA accumulation decreases (low ratio PGA/RuBP and PGA). At saturated light conditions (2000 μmol photons $m^2 S^{-1}$) photosynthesis is limited by Rubisco activity only and therefore PGA/RuBP significantly increases.
Figure 4A:
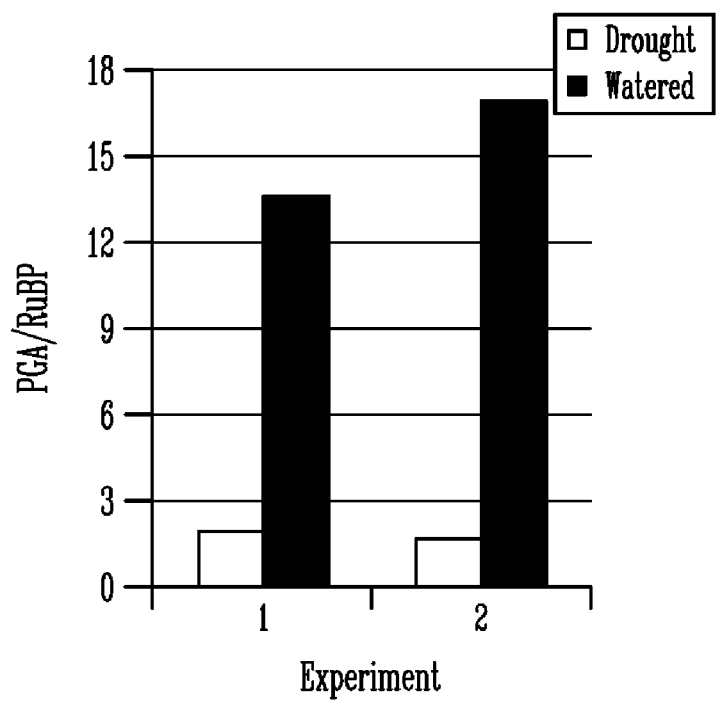
FIG. 4. Effect of drought stress on the ratios of PGA/RuBP and 2-A/PGA in tobacco leaves. Tobacco plants were grown for two weeks at 25° C. under 350 μmol photons $m^{-2} S^{-1}$ light intensity and 30% humidity under well-watered conditions. The drought treatment started by withholding water and samples were collected after few days when the leaves started welting. Three plants grown under normal and drought stress were sampled and analyzed for PGA, RuBP and 2-A ratio. Drought causes reduced stomatal opening that reduces $CO_2$ concentration while remains high $O_2$ concentration. As a result, Rubisco carboxylation reaction is reduced (A; low PGA/RuBP) and Rubisco oxygenation activity is promoted (B; high 2-PA/PGA).
Figure 4B:
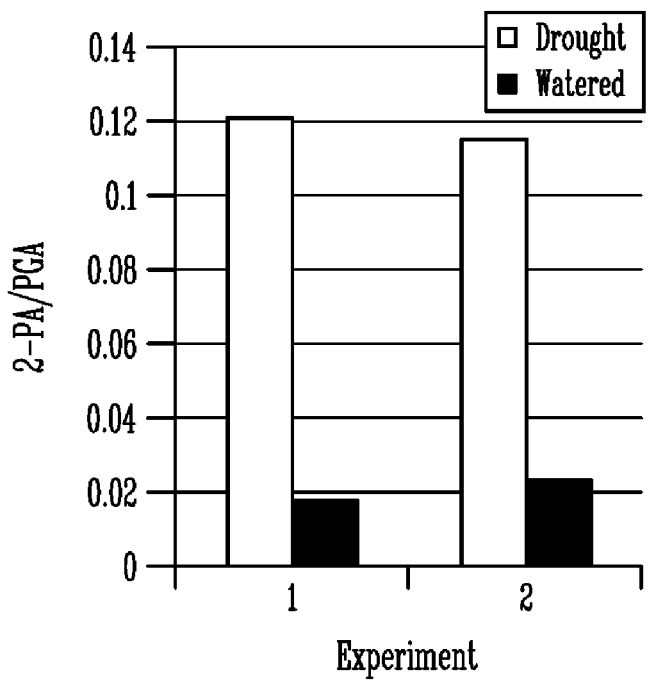
Figure 5A:
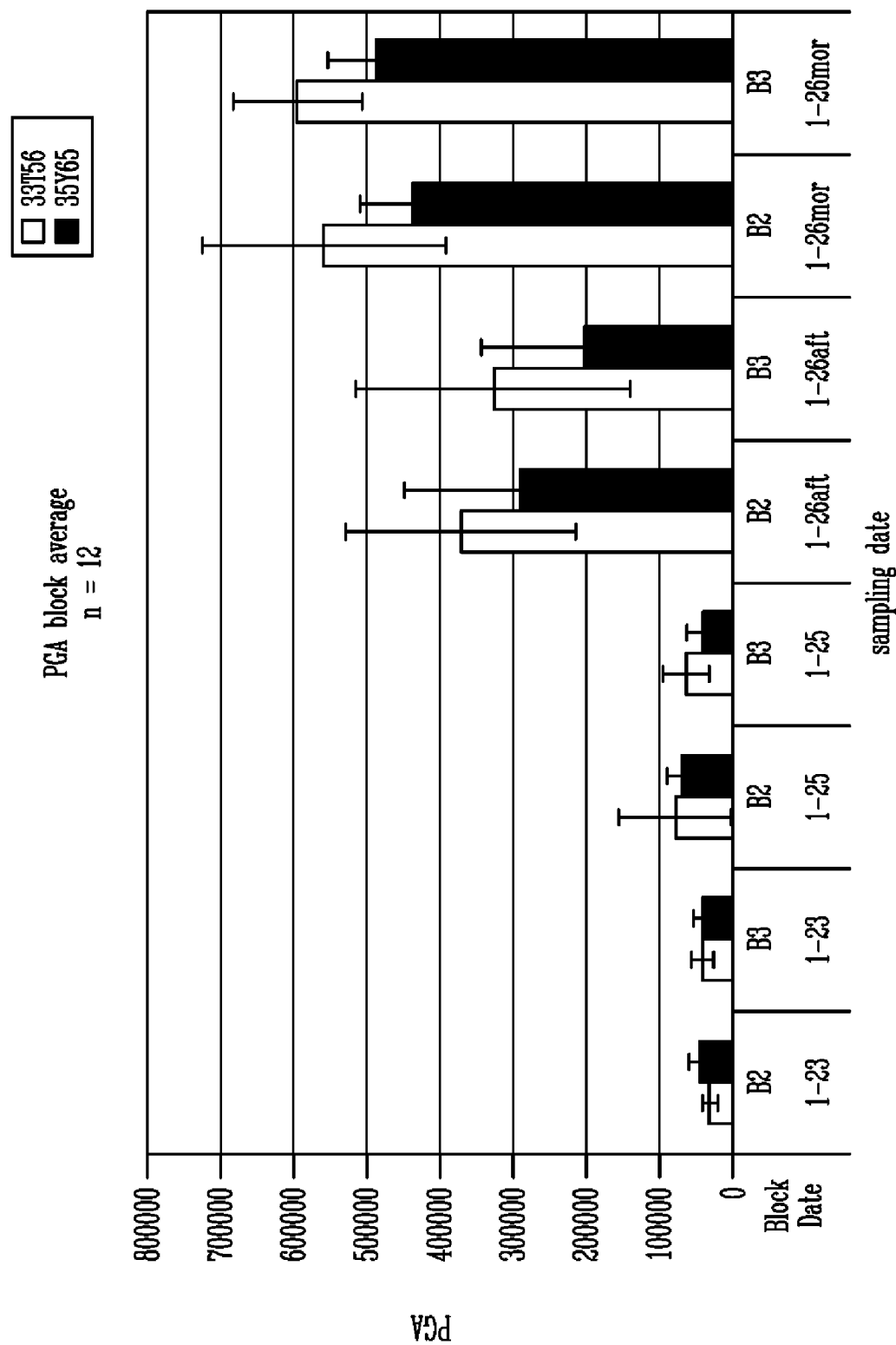
FIG. 5. Effect of drought stress on the photosynthetic performances of the hybrids 33T56 and 35Y65 grown in field. Mature plants were exposed to drought stress treatment for three weeks. Samples were collected at the end of the drought treatment (1-23) and during the recovery from the stress (after two days 1-25). Samples from well watered hybrids were collected at the morning and afternoon (1-26 aft and 1-26 mor respectively). PGA levels (A) and chlorophyll fluorescence levels monitored by chlorophyll flluorimeter (B) indicated low photosynthetic performances during the drought stress treatment. PGA measurements were more sensitive at high photosynthetic levels and monitored the inhibition of photosynthesis caused by elevated temperatures (5A; 1-26 aft and 1-26 mor compared with 5B; 1-26 aft and 1-26 mor). The overall photosynthetic performances monitored by PGA levels showed similar pattern to the photosynthetic performances detected by the chlorophyll flluorimeter (C).
Figure 5B:
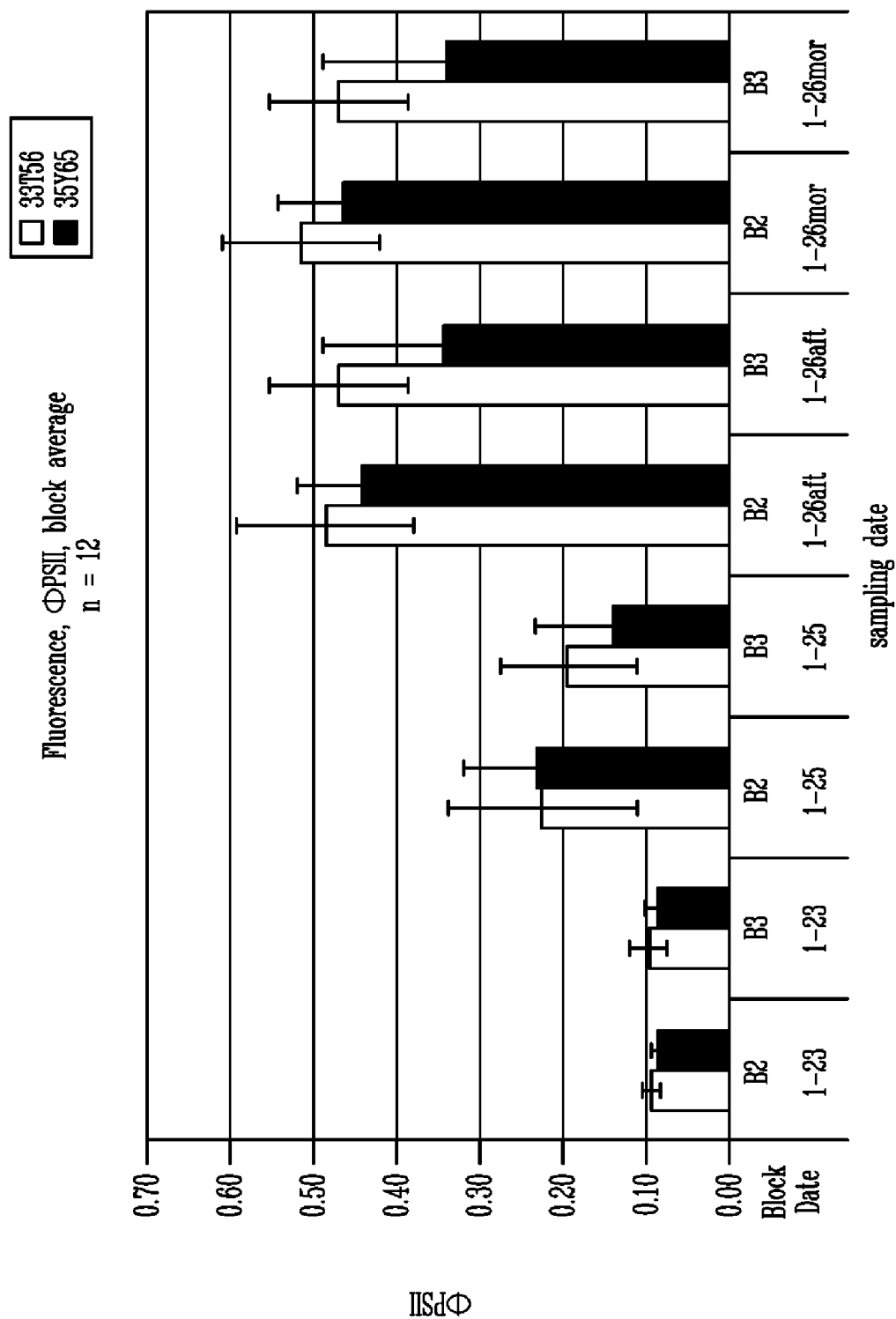
Figure 5C:
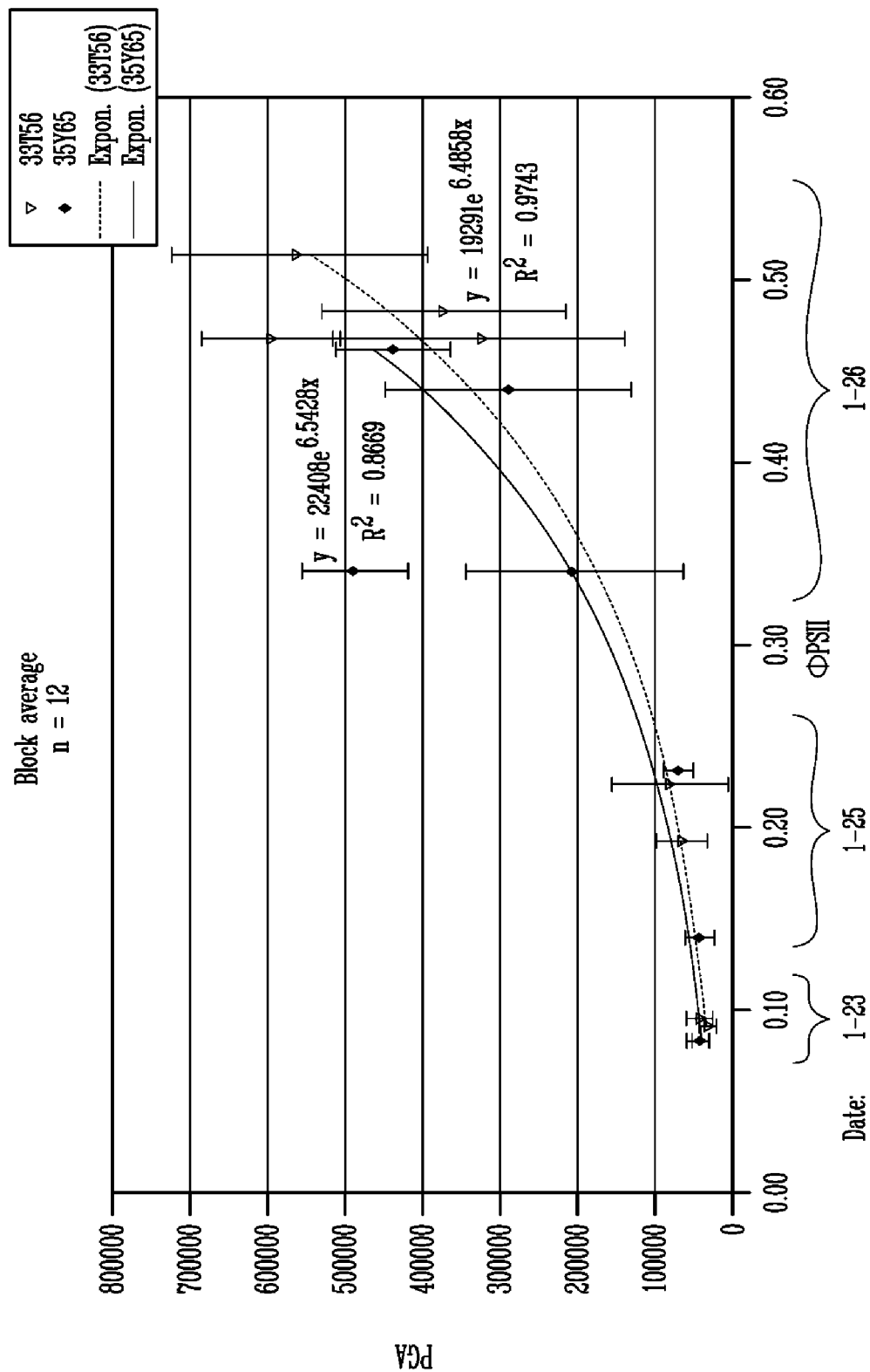

The present invention relates to methods and systems to evaluate in planta Rubisco performance or photosynthetic performance of a plant. Each Rubisco carboxylation reaction generates two molecules of PGA from one molecule of RuBP and its oxygenation reaction generates equal molecules of PGA and 2-A. The pool level of RuBP, PGA and 2-A and their ratios are dynamically affected by: (1) Rubisco catalytic activity, (2) the activity of Rubisco activase (RCA) that activates Rubisco and maintains Rubisco at high activation state, (3) the $CO_2/O_2$ ratio at Rubisco site that can be affected by the change of stomata opening during drought stress, (4) enzymes that are involved in RuBP regeneration in the Calvin cycle and (5) other components of the photosystem (FIG. 1). To analyze Rubisco activity in planta the present inventors developed a novel method and system that directly measures RuBP, PGA and 2-A under different conditions and at fairly low levels. Using the systems and methods of the present invention, as low as 10 parts per million (ppm) RuBP, PGA and 2-A in fresh weight leaves may be detected and as little as a 80 μm² leaf disc may be sufficient to detect RuBP, PGA, or 2-A. Advantageously, the methods of the invention may be conveniently practiced without the need for radiolabeling and, unlike other methodologies, the methods and systems of the invention can be used to detect RuBP, PGA, and 2-A directly in a high throughput fashion. The methods and systems of the present invention allow for the analysis and screening of plants for photosynthetic performances directly related to Rubisco activity and regulation.

To evaluate Rubisco activity and to determine plant photosynthetic performance, the present inventors have developed a novel method for direct detection of low levels of RuBP, PGA and 2-A in planta. Furthermore, the present inventors believe that they are the first to discover a method for direct, simultaneous detection of 2-A with PGA and RuBP in planta. The present invention is based in part on the surprising discovery that ion pairing high performance liquid chromatography (HPLC) may be used to isolate RuBP, PGA, and 2-A from a photosynthetic cellular extract and mass spectrometry may be used to detect and measure levels of any of the isolated RuBP, PGA, and 2-A and/or combinations of RuBP, PGA, and 2-A.

Although RuBP and PGA or 2-A can be separated using HPLC anion exchange chromatography using salt gradient elution (Uemura et al, Plant Cell Physiol. 1996, 37: 325-331 and Suzuki K et al, Plant Cell Physiol. 1999, 40:792-799), ion exchange chromatography is usually not compatible with mass spectrometry detection.

According to the invention, a RuBP, PGA, or 2-A molecule or combinations thereof can be resolved from the complexed components of a photosynthetic cellular extract by any of a variety of methods including chromatographic and spectrometric methods. The present invention employs techniques, for example, reverse phase HPLC and tandem mass spectrometry that are routine using analytical methods of chemistry and biochemistry and that are well within the skill of the art. Such techniques are known and explained fully in the literature. See, e.g. "Mass Spectrometry: A Foundation Course", K. Downard, Royal Society of Chemistry, UK, 2004; "An Introduction to Biological Mass Spectrometry", C. Dass, Wiley, USA, 2002; "Ionization Methods in Organic Mass Spectrometry", A. E. Ashcroft, Analytical Monograph, Royal Society of Chemistry, UK, 1997; "HPLC: A Practical User's Guide" 2nd edition, M. McMaster, Wiley, USA, 2006; "LC/MS: A Practical User's Guide" M. McMaster, Wiley, USA, 2005; and "Modern HPLC for Practicing Scientists", M W Dong, Wiley, USA, 2006.

Figure 6:
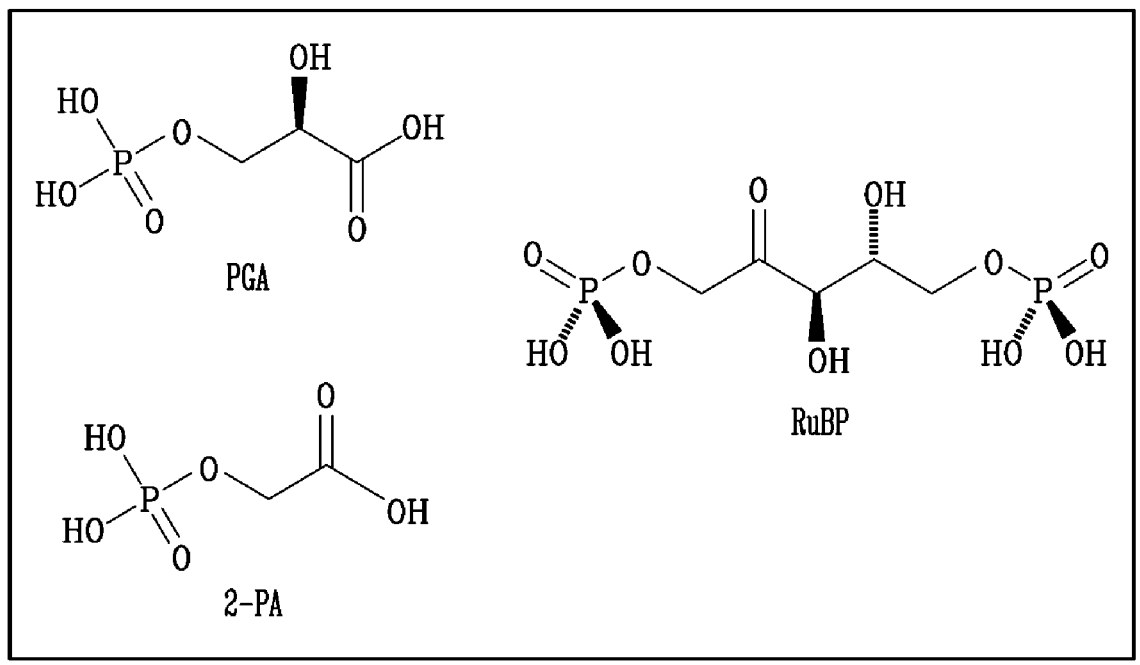
FIG. 6. The molecular structures of PGA, RuBP and 2-A.
Figure 7:
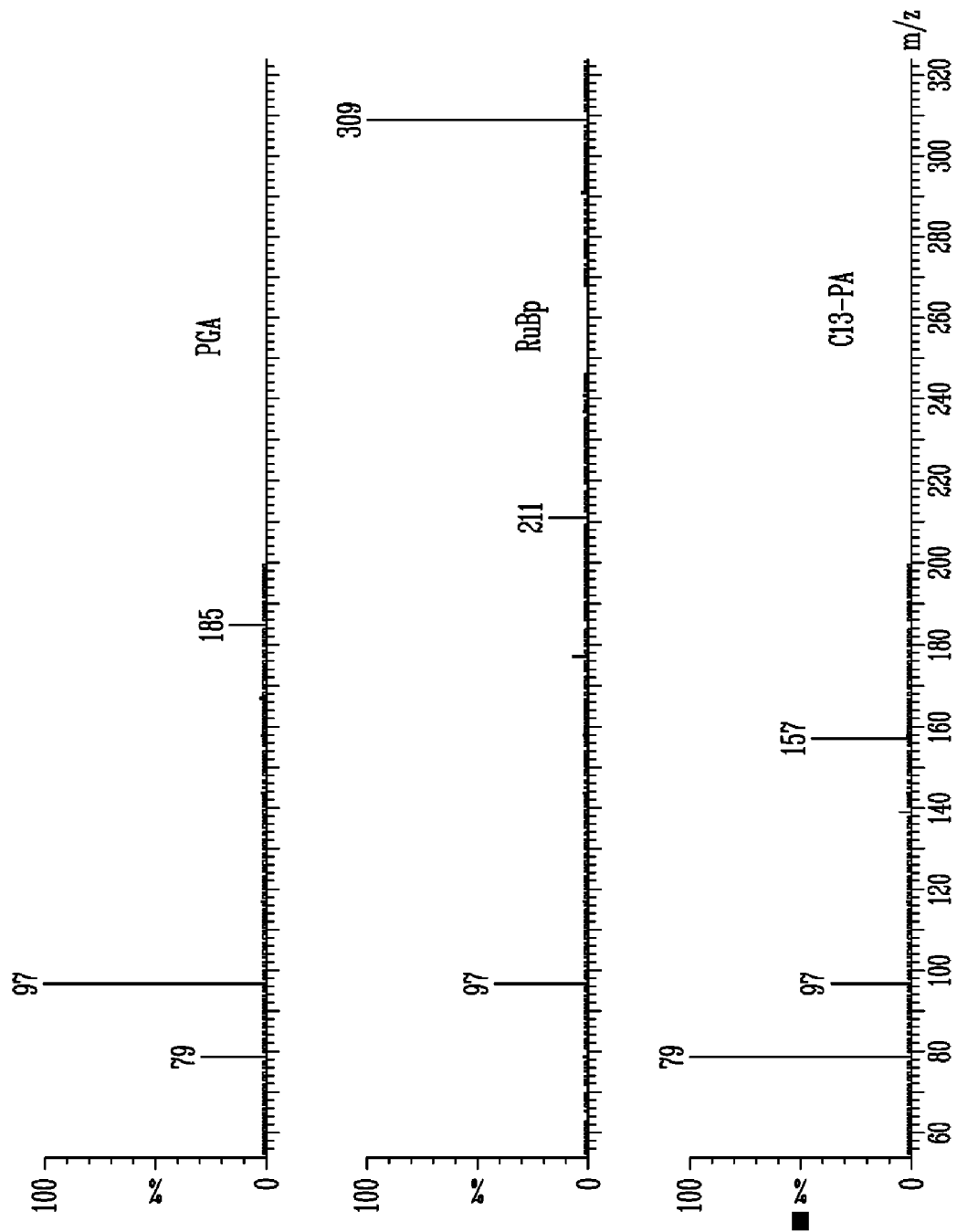
FIG. 7. MS/MS daughter-ion spectra of PGA, RuBP and $^{13}$C-labeled 2-A in negative electrospray mode. The precursor ions of PGA, RuBP and $^{13}$C-labeled 2-A were detected at 185 m/z, 309 m/z and 157 m/z, respectively. The most abundant daughter-ions, at 97 m/z, 97 m/z and 79 m/z were chosen to monitor the precursor-daughter ion transition for PGA, RuBP and $^{13}$C-labeled 2-A respectively.
Figure 8:
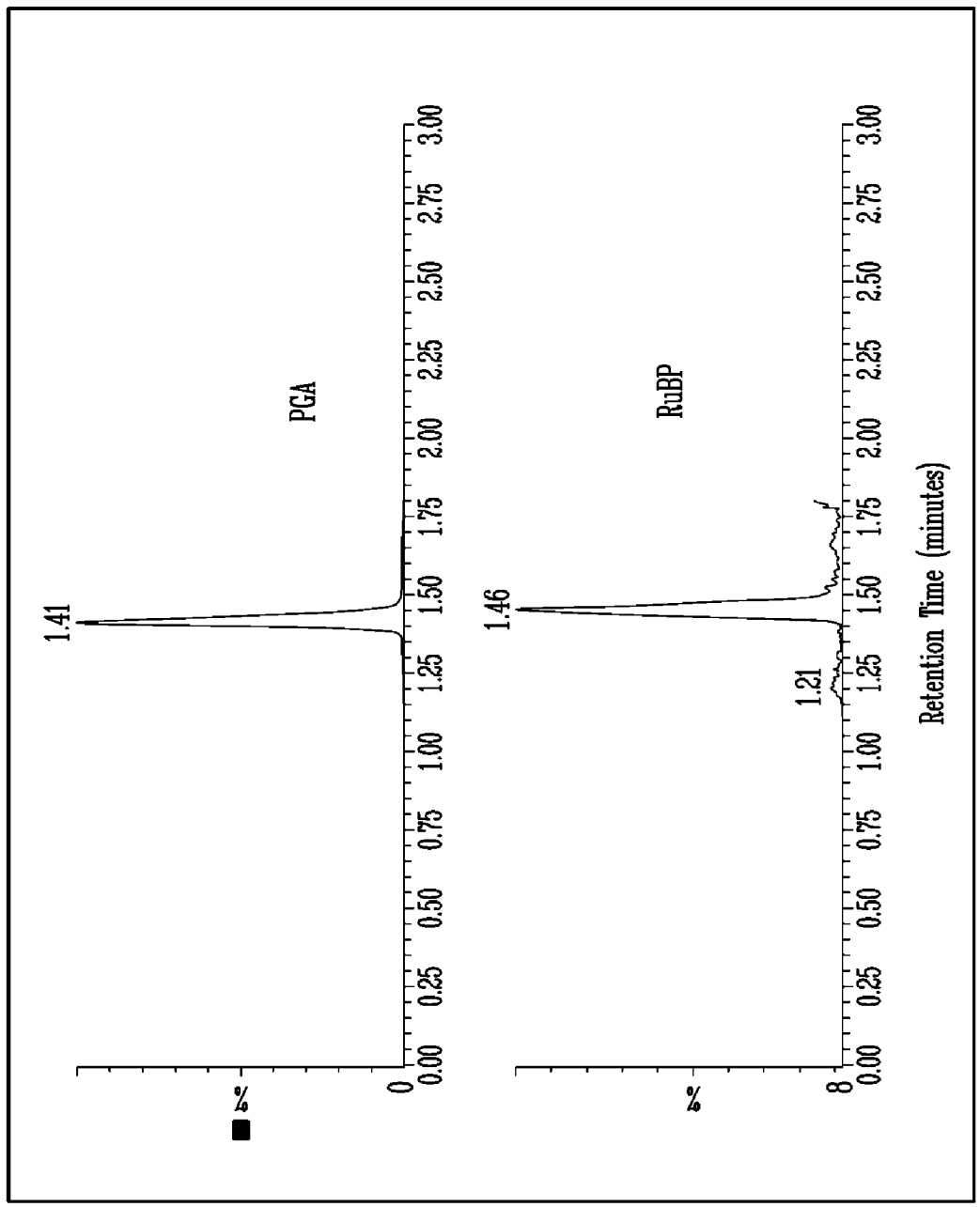
FIG. 8: Representative ion-pairing HPLC chromatograms when PGA and RuBP are monitored simultaneously.
Figure 9:
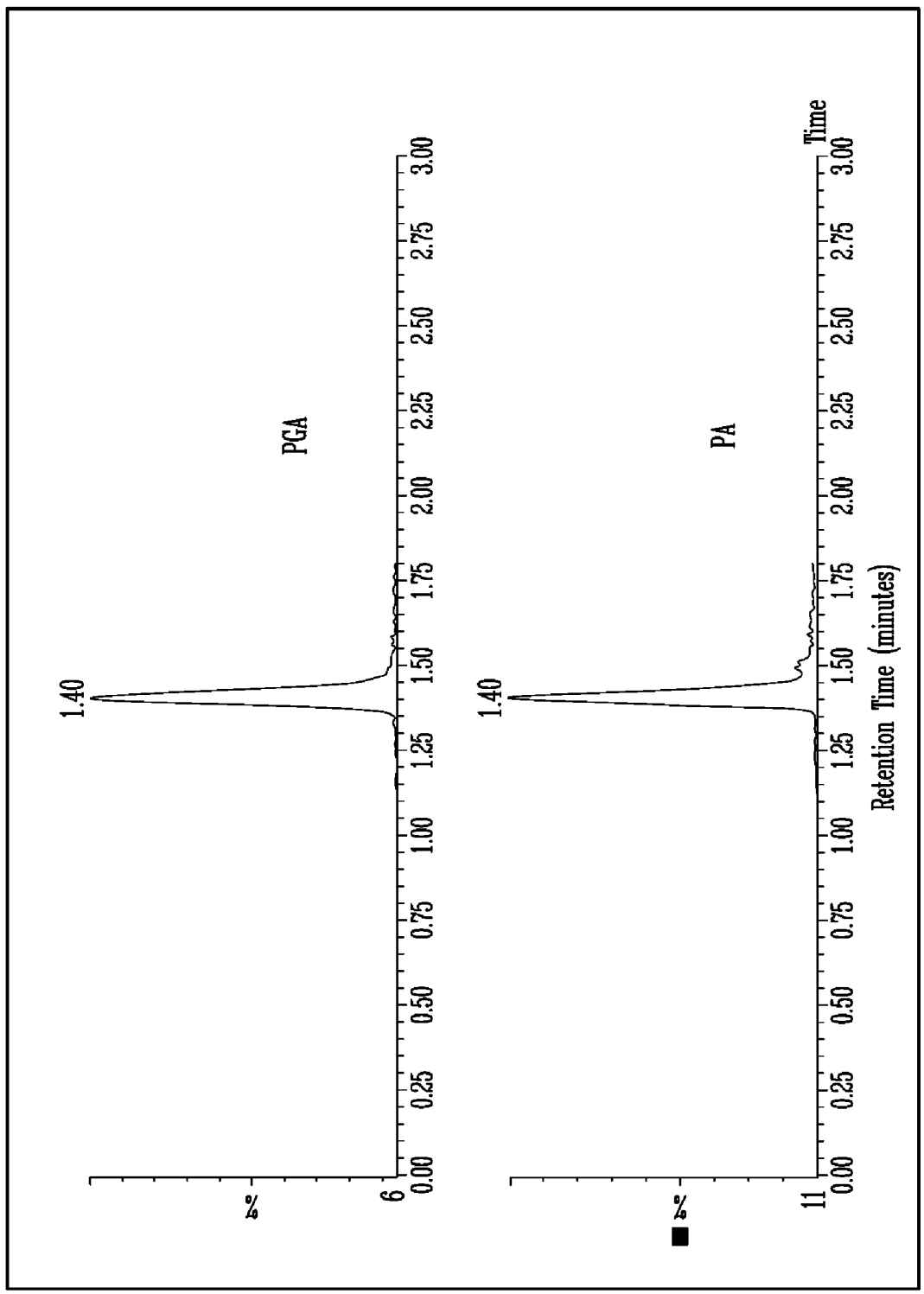
FIG. 9: Representative ion-pairing HPLC chromatograms when PGA and 2-A are monitored simultaneously.

In one embodiment, the present invention provides a method for resolving and measuring the level of RuBP, PGA, or 2-A or combinations thereof in a photosynthetic cellular extract. In one aspect, the method includes loading a photosynthetic cellular extract from a plant into a reverse phase chromatography column and performing reverse phase high performance liquid chromatography on the extract. In another aspect, the method includes detecting and measuring the separated RuBP, PGA, or 2-A or combinations thereof using tandem mass spectrometry. The molecular structures of RuBP, PGA, and 2-A and their daughter ion mass spectra are shown in FIGS. 6 and 7, respectively.

As used herein, the term "resolving", "resolved" or variations thereof means sufficiently separating a RuBP, PGA, or 2-A molecule from other molecules to allow detection of a level of the RuBP, PGA, or 2-A. The methods of the invention are useful for determining a level of a RuBP, PGA, or 2-A in a photosynthetic cellular extract. The term "level," as used herein, refers to an amount or concentration of the RuBP, PGA, or 2-PA, for example, in a photosynthetic cellular extract. It is understood that a level can be an absolute level such as a molar concentration or weight or a relative level such as a percent or fraction compared to one or more of RuBP, PGA, or 2-A molecules in one sample, for example, a photosynthetic cellular extract from a plant under abiotic stress, as compared to another sample, for example, a photosynthetic cellular extract from a plant not subjected to the abiotic stress.

As used herein, the term "increased photosynthetic performance" refers to a plant that has increased Rubisco activity, such as increased photosynthetic rate, increased carboxylase activity and/or specificity, for example, increased RuBP carboxylase rate, decreased RuBP oxygenase rate, increased $K_m$ for $O_2$, decreased $K_m$ for $CO_2$, decreased ratio of $K_m$ for $CO_2$ to $K_m$ for $O_2$, and/or velocity of incorporating $O_2$ to $CO_2$ compared to another plant, for example, a control plant. See U.S. application Ser. No. 12/102,639 herein incorporated by reference in its entirety. It is known that a plant's photosynthetic performance associated with Rubisco activity may be determined in any number of ways, for example, on the basis of the levels of RuBP, PGA, or 2-A or ratios of PGA/RuBP or 2-A/PGA present in a photosynthetic part of a plant, such as a leaf. (see, He et al., "Ribulose-1,5-Bisphosphate Carboxylase/Oxygenase Activase Deficiency Delays Senescence of Ribulose-1,5-Bisphosphate Carboxylase/Oxygenase but Progressively Impairs Its Catalysis during Tobacco Leaf Development", *Plant Physiol.* 115:1569-1580 (1997); Cen, Yan-Ping et al., "The Regulation of Rubisco Activity in Response to Variation in Temperature and Atmospheric $CO_2$ Partial Pressure in Sweet Potato: *Plant Phys.*, 139:979-990 (2005)).

In one aspect, a method of the present invention includes obtaining a photosynthetic cellular extract. A photosynthetic cellular extract useful in a method of the invention can be any photosynthetic cellular extract that contains one or more RuBP, PGA, or 2-A molecules. Cellular extracts can be prepared from any cell or tissue that is photosynthetic or obtained from a commercial source. It is understood that additional exogenous RuBP, PGA, or 2-A can be added, if desired, to a photosynthetic cellular extract or a solvent for use in determining a standard curve for quantification or for optimizing detection conditions. A photosynthetic cellular extract containing RuBP, PGA, and/or 2-A may be prepared from a plant or plant material, using any number of methods, for example, leaf punching and methanol extraction. See Example 1. Such techniques are routine and will be known to those of ordinary skill in the art. The present inventors have found that as little as an 80 $\mu m^2$ leaf disc may be sufficient to detect the RuBP, PGA, or 2-A. In one aspect, the photosynthetic cellular extract may be placed in a multi-well plate, for example, a 96 well plate, and optionally diluted with an appropriate solution, such as mobile phase A, prior to introduction into a HPLC column. The use of a multi-well plate facilitates the number and speed of plants that can be assayed for levels of RuBP, PGA, or 2-A.

In one aspect, the method includes a combination of two solutions, referred to herein as mobile phase A and mobile phase B, that have differing amounts of organic solvents. Both mobile phases comprise an organic solvent. Typically, the percentage of organic solvent in mobile phase A will be lower than the percentage of the organic solvent in mobile phase B. Any suitable organic solvent may be used and includes but is not limited to acetonitrile or methanol or combinations thereof. In one aspect, mobile phase A is 10% v/v acetonitrile in water. In another aspect, mobile phase B comprises 90% v/v acetonitrile in water.

In one aspect, the method includes an ion pairing reagent, such as, but not limited to, N,N-dimethylhexylamine or diethylamine. Suitable ion pairing reagents including volatile ion pairing reagents are known to those skilled in the art. In one aspect, the ion pairing reagent is 0.2% v/v N,N-dimethylhexylamine. The ion pairing reagent may be present in one or both mobile phases, mobile phase A and/or B, to help retain RuBP, PGA, or 2-A or combinations thereof on the column. Formic acid may be used to adjust the pH of both mobile A and B, for example, to about 8 (0.04% v/v). Other acids such as acetic acid may also be used to adjust pH levels.

In another aspect, the method includes eluting the column with a linear gradient of organic solvent (i.e., mobile phase B) to elute the RuBP, PGA, or 2-A or combinations thereof. Elution can be performed using one or more gradients or isocratic conditions, with gradient conditions preferred to reduce the separation time and to improve resolution. Generally, the gradient comprises solvents from very low organic content (from about 0%) to very high organic content (up to 100%). A particularly preferred method involves the use of a linear gradient of holding 5% mobile phase B for 0.5 min, then increasing to 50% mobile phase B in 1 min at a flow rate of 0.3 ml/min. In one aspect, the chromatography column comprises a $C_{12}$ silica-derivatized stational phase. In one aspect, the column is a Synergy Max-RP column (Phenomenex, Torrance, Calif.). In one aspect, the column dimension is 50×2 mm. It is understood that any other reverse phase chromatography column suitable for resolving RuBP, PGA, or 2-A may be used in the methods or systems of the present invention. The columns may vary in diameter, length or both, for example, to accommodate larger or smaller sample sizes. Flow rates can vary, without limitation, from 0.1 to 1 ml/minute. As demonstrated herein, the flow rate for the mobile phase was 0.3 ml/minute. However, the flow rate of the mobile phase can be altered as desired. A slower flow rate, such as 1 $\mu$l/minute, 10 $\mu$l/minute or 100 $\mu$l/minute, can be used, for example, with a smaller column or a nanocolumn or to increase RuBP, PGA, or 2-A retention times. Alternatively a faster flow rate, such as 2 ml/minute or 10 ml/minute, can be used, for example, with a larger column or to decrease RuBP, PGA, or 2-A retention times.

As demonstrated herein, chromatographic resolution of RuBP, PGA, or 2-A can be performed by passing a mixture of RuBP, PGA, and/or 2-A from a photosynthetic cellular extract through a $C_{12}$ reverse phase chromatography column with a linear gradient comprising holding 5% mobile phase B for 0.5 min, then increasing to 50% mobile phase B in 1 min to separate and elute the RuBP, PGA, or 2-A or combinations thereof (Example 2). In one aspect, mobile phase A is 0.2% (v/v) dimethylhexylamine 0.04% (v/v) formic acid and 10% (v/v) acetonitrile in water. In another aspect, mobile phase B is 0.2% (v/v) dimethylhexylamine 0.04% (v/v) formic acid and 90% (v/v) acetonitrile in water.

Column size, flow rates, and conditions (e.g. pH, choice of buffer) are selected in accordance with standard techniques and may be optimized for both chromatographic separation and electrospray ionization efficiency. Those skilled in the art will appreciate, and readily accommodate, without undue experimentation, that adjusting flow rates and gradients for substitution of various A/B gradient setups, such as substituting water/acetonitrile for water/methanol. Even so, specific percentages, times and flow rates will readily be selectable for various choices of solvents, all in accordance with the teachings disclosed herein.

It is understood that such analytical techniques such as HPLC can be combined with other means for detecting at least one RuBP, PGA, or 2-A or combinations thereof in a photosynthetic cellular extract. Accordingly, RuBP, PGA, or 2-A may be resolved by HPLC and analyzed by mass spectrometry. A method for determining a level of RuBP, PGA, or 2-A or combinations thereof in a photosynthetic cellular extract by mass spectrometry is provided.

The mass spectrometry detection may be conducted with a single quadrupole mass spectrometer, a "tandem-in-space" mass analyzer such as a "triple quadrupole" mass spectrometer and "tandem-in-time" mass analyzer such as a Paul ion trap or Fourier Transform Ion Cyclotron Resonance (FT-ICR). In a single quadrupole mass analyzer, the ionized sample undergoes "upfront" collisionally induced dissociation (CID) between the atmosphere-to-vacuum interface and the mass analyzer. Product ions related to the compounds of interest and unfragmented ions are passed through the mass filter for analysis and detection. Since only a single mass analyzer is used, the selectivity and specificity of this technique is limited. Using triple quadrupole mass spectrometer, the first mass filter (Q1) selects the molecular ion of interest while the second mass filter selects specified product or fragment ions. Between these stages of mass filtration, the precursor molecular ions selected by the first stage undergo collisionally induced dissociation (CID) to produce product or fragment ions. The particular molecular and fragment ions of interest will, of course, vary with the structure of the target of interest. Accordingly, in one aspect, the method of the invention further comprises the using of tandem mass spectrometry.

In one aspect, the method includes detecting and measuring RuBP, PGA, or 2-A or combinations thereof using tandem mass spectrometry in the negative ionization mode. The precursor ions of each analytes may be determined from spectra by infusing the standard reference compounds. When 2-PA reference compound is not available as a standard, home-synthesized $C^{13}$-2-PA may be used instead and mass/charge ratios of non-labeled 2-A is calculated accordingly. Each precursor ions may be subjected to CID using a neutral gas such as argon or intrigen to obtain their daughter-ion spectra (FIG. 7). The most abundant product ion is selected and other parameters may be optimized for the multiple reaction monitoring (MRM). Accordingly, quantitative analysis of RuBP, PGA, or 2-A may be based on the MRM transitions of 309→97, 185→97 or 155→79, respectively.

Although these three analytes were analyzed in the negative ionization mode, it is understood that they may be detected in the positive mode if they can form positive adduct ions with protons or ammonium and can be monitored using specific MRM transitions. It is expected that volatile ion-pairing reagents such as dimethylhexylamine are needed for the HPLC separation. Therefore other buffers like ammonium acetate or ammonium formate can be used.

Integration of chromatogram peak areas may be performed with any suitable program, for example, using Masslynx software (Micromass, UK). Often these programs accompany the mass spectrometer instrument. The peak areas may be compared to the areas of a set of known standards for absolute quantitation if desired. For relative quantitation or semi-quantitation of RuBP, PGA or 2-A between different samples, the peak area ratios, for example PGA/RuBP and/or 2-A/PGA, may be used, although the peak area ratios do not in all cases equal the concentration ratios.

As further disclosed herein, RuBP, PGA and 2-A levels were determined in photosynthetic cellular extracts from maize and tobacco plants subjected to differing abiotic stresses, such as heat and drought stress, and their respective levels of RuBP, PGA and 2-A and/or ratios of PGA/RuBP or 2-A/PGA compared. Thus, a method of the invention can be used to monitor or determine the photosynthetic performance of a plant. The method of this invention is reliable, rapid, simple and amenable to high throughput, using, for example, a 96 well plate. The HPLC has a runtime of approximately 2-minutes and consequently throughput of more than 192 plants a day can be screened.

As disclosed herein, the present invention provides for methods and systems to determine levels of RuBP, PGA, or 2-A in photosynthetic cellular extracts. In one aspect, the plants are subjected to abiotic stresses. As disclosed in Examples 1 and 2, the method and system may include preparation of an extract from a plant and direct injection of the resulting extract into an HPLC system composed of a $C_{12}$ reversed phase column with formic acid and acetonitrile in water as the mobile phase.

Methods of the present invention may be used to screen for and identify plants that have increased photosynthetic performance. The invention also contemplates that method may be used to screen and identify plants that are tolerant to abiotic stresses, in particular, drought and heat. As described above, the method includes introducing a photosynthetic cellular extract from a first plant into a reverse phase chromatography column. In another aspect, the method includes performing reverse phase high performance liquid chromatography on an extract to resolve RuBP, PGA, or 2-A or combinations thereof. In yet another aspect the method includes detecting the separated RuBP, PGA, or 2-A or combinations thereof using mass spectrometry. In one aspect, mass spectrometry is performed using a mass spectrometer that is a tandem mass spectrometer. The method may also include obtaining a photosynthetic cellular extract from one or more plants.

In another aspect, the method includes determining a level of RuBP, PGA, or 2-A and/or a ratio of PGA/RuBP or 2-A/PGA in the photosynthetic cellular extract from the plant. In another aspect, the method includes comparing the level of RuBP, PGA, or 2-A and/or the ratio of PGA/RuBP or 2-A/PGA detected in the sample, for example, from a photosynthetic cellular extract, of a first plant to the level of RuBP, PGA, or 2-A and/or the PGA/RuBP ratio or the 2-PA/PGA ratio detected in the sample, for example, from a photosynthetic cellular extract, of a second plant. A first plant that has a level of PGA and a PGA/RuBP ratio that are greater than the level of PGA and PGA/RuBP ratio from a second plant is indicative of the first plant having increased photosynthetic performance compared to the second plant. A first plant that has a level of 2-A and ratio of 2-PA/PGA that are less than the level of 2-A and the ratio of 2-PA/PGA from a second plant is indicative that the first plant has increased photosynthetic performance compared to the second plant.

In other aspects, the present methods or systems can be used to identify a plant that has increased tolerance to an abiotic stress. In one aspect, the abiotic stress is drought, cold temperatures, salt, osmotic stress, frost or freeze, high heat temperatures, low light, oxidative stress, and chemical stress as well as stress by other environmental stresses, such as UV-B, ozone, photooxidation, herbicide, pathogen, or other stresses that also involve oxidative stress damage and the like. For example, the tolerance of a plant to dehydration, salinity, temperature stress, environmental stress or a pathogen may be determined by its photosynthetic performance using the methods and systems described herein.

By comparing the level of RuBP, PGA or 2-A and/or ratio of PGA/RuBP or 2-PA/PGA or combinations thereof in a plant subjected to at least one abiotic stress to the level of RuBP, PGA or 2-A or ratios of PGA/RuBP and 2-A/PGA in a plant not subjected to an abiotic stress, one can identify a plant with an increased tolerance to the abiotic stress. For example, plants can be monitored under various stress conditions, such as drought, and compared to control plants. A "control" or "control plant" provides a reference point for measuring changes in a phenotype of the subject plant, for example, levels of RuBP, PGA or 2-A or changes thereof. A control plant may comprise, for example a wild-type plant, i.e., of the same genotype as the subject plant or a wild-type plant, i.e., of the same genotype as the subject plant that is not exposed to stress conditions. In some instances, the control plant may be a transgenic plant, i.e., of the same genotype as the subject plant or a transgenic plant, i.e., of the same genotype as the subject plant that is not exposed to stress conditions. One skilled in the art will be able to select the appropriate control. Using methods or systems of the present invention, one skilled in the art would be able to screen thousands of different plants, for example, for their ability to tolerate abiotic stresses.

The methods of the present invention are useful for a variety of applications. As discussed, the methods and systems of the present invention permit the identification of plants with increased photosynthetic performance and/or increased tolerance to abiotic stresses, including drought and heat tolerance. Identification of those plants, in turn, can be used to understand the pathways or genes involved in any particular tolerance.

The present invention provides for a high throughput system for identifying a plant with increased photosynthetic performance or increased Rubisco activity. In one aspect, the system includes introducing into a multi-well plate a photosynthetic cellular extract from at least one plant. In one aspect, the plant is subjected to an abiotic stress. In another aspect, the system includes introducing the photosynthetic cellular extract into a reverse phase chromatography column via an automated solid phase extraction system. In another aspect, the system includes performing reverse phase high performance liquid chromatography (HPLC) on the extract to detect and measure the levels of RuBP, PGA, or 2-A or combinations thereof to generate HPLC eluates comprising RuBP, PGA, or 2-A or combinations thereof. In another aspect, the system includes introducing the eluates into a tandem mass spectrometer. In one aspect, the mass spectrometer is a triple quadrapole mass spectrometer. In another aspect, the system includes detecting and measuring levels of RuBP, PGA, or 2-A or combinations thereof with tandem mass spectrometry. In another aspect, the system includes determining a ratio of PGA/RuBP and/or 2-A/PGA.

The system may include any aspect described above with respect to the methods of the present invention, for example, the use of various solvents, such as mobile phase A, mobile phase B, ion pairing reagents, gradients, mass spectrometry, and its various detection modes, such as negative or positive ionization modes or multiple reaction monitoring.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Example 1

Sample Preparation

RuBP, PGA and 2-A were extracted according to the protocol described below:
1. Freeze 1 to 3 leaf discs (1 cm diameter) in liquid $N_2$ using the single leaf punch device.
2. Dry the leaf discs in 2 ml tubes over-night in the lyophilizer.
3. Add two stainless steel grinding beads (5/32") into each tube and homogenize the leaf discs for 1.5 min (310 strokes/min) using the Spex CertiPrep GenoGrinder 2000.
4. Add 300 μl 50% Met-OH and shake the tubes for 30 sec (310 strokes/min) using the Spex CertiPrep Geno-Grinder 2000.
5. Shake the tubes for 10 min at room temperature.
6. Centrifuge for 10 min at 13,000 rpm.
7. Transfer 100 μl to 1.5 ml tube and centrifuge for 5 min at 13,000 rpm.
8. Transfer 50 μl to 96-deep well plate and dilute the sample by adding 450 μl of mobile phase A (see below) for liquid chromatography and tandem mass spectrometry (LC-MS/MS) analysis.

Example 2

HPLC/MS-MS Analysis

RuBP, PGA and 2-A were separated by reverse phase chromatography using following conditions:
HPLC column: Synergy Max-RP column (50×2 mm from Phenomenex);
Flow rate: 0.3 ml/min;
Mobile phase A: 0.2% (v/v) dimethylhexylamine and 0.04% (v/v) formic acid in 10% (v/v) acetonitrile;
Mobile phase B: 0.2% (v/v) dimethylhexylamine and 0.04% (v/v) formic acid in 90% (v/v) acetonitrile;
Gradient: 5% B held for 0.5 min, then 50% B in 1 min. Wash column for about 0.8 min.;
Injection volume: 5-10 μl from sample in 96 well-plate described in Example 1.

RuBP, PGA and 2-A were detected separately by negative electrospray tandem mass spectrometry in the multiple reaction monitoring (MRM) mode using a triple quadrupole mass spectrometer from Waters (Quattro Ultima). The MS/MS reactions were selected to monitor the transitions of 309->97 for RuBP, 185->97 for PGA and 155->79 for 2-PA, respectively.

Example 3

Abiotic Stress for Tobacco and Maize Plants

Maize plants were grown at 27° C. under 16/8 hours light (400 μmol photons $m^{-2} s^{-1}$) dark regime and 40% humidity for three weeks. Three samples (each contains three leaf-discs from three independent plants) from plant grown under normal temperature were collected (time=0). Maize plants were then transferred to the growth chamber for heat treatment (35° C. or 40° C.) under the same light/dark regime and humidity. Three samples as described for the normal growth conditions were collected after 30, 60, 120 and 180 min and analyze for PGA and RuBP levels.

Tobacco plants were grown for two weeks at 25° C. under 16/8 hours light (350 μmol photons $m^{-2} s^{-1}$) dark regime and 30% humidity under well watered conditions. The drought treatment was started by withholding water under the same conditions described above. Control plants were kept under well-watered conditions. Samples were collected after three days when the leaves of drought treatment plants exhibited welting phenotype. Three control plants and three drought stressed plants were sampled and analyzed for PGA, RuBP and 2-A levels.

Example 4

Examples of Stress Conditions

Prophetic

Plants, including genetically and non-genetically modified plants, may be subjected to artificial environments to simulate abiotic stresses, for example, heat, cold, drought, light or limited water conditions, a combination of drought and heat, or to salinity stress.

To determine a plant's photosynthetic performance under cool conditions, seeds may be germinated under conditions similar to the standard cold germination tests used in the seed industry. Alternatively, seeds may be planted under cool seed bed conditions made cool by artificial environments or naturally cool seed beds in the field. Young transgenic seedlings may be grown at a low temperature, such as about 13° C., during the light and 13° C. during the dark period. Seeds may be planted in 96-pod flats containing greenhouse soil medium and initially watered with Seplex water for the first day after planting. Seedlings may be germinated in the greenhouse. After the initial watering, seedlings may be watered with 85 ppm 20:10:20 fertilizer water. Once plants reach the V3 stage (approximately 10-14 days), plants may be moved to a growth chamber and subjected to a chilling regimen of 16/8 hour light/dark cycle, where day/night temperatures are maintained at 15° C. light/13° C. dark, under constant humidity. The seedlings may receive bottom water with 85 ppm 20:10:20 fertilizer water, keeping the seedlings well-watered. Seedlings may be subjected to chilling conditions for the next 16 days. The seedlings may be scored for stress by observing visual yellowing at 4, 8, 12 and 16 days into the stress period and also recording chlorophyll fluorescence using the Hansatech FMS2 chlorophyll fluorescence meter (Hansatech Instruments Ltd). Leaf discs may be used to determine ROS accumulation due to photo-oxidative damage under low temperature combined with high light. Leaf discs may be used to determine levels of RuBP, PGA, and/or 2-A as indicative of photosynthetic performance or activity of the plant under abiotic stress. These may be taken after 8 hours light. Thus, plant performance and tolerance of the plant to the abiotic stress may be assessed in the plant relative to a control plant. It is to be understood that the control plant may be non-stressed and/or non-transgenic as appropriate. Additional physical characteristics of the subject plant and the control plant, for example, growth or biomass, may be assessed using techniques known to one skilled in the art.

Plants may also be assayed for increased freezing tolerance at the seedling stage as well as late season periods. These assays are preferably done in artificial environments to simulate frost or freeze events. In addition, seeds may be planted outside during times when the natural environment would impose the stress, e.g., at times when frost is present.

Plants may also be assayed in artificial drought-stress environments in pot-based studies or under managed drought-stress conditions in the field in order to determine if the plant has resistance or tolerance to drought. Plants may be subjected to well-watered conditions (control) and to drought-stressed conditions. Plants may be screened at the T1 stage or later. Stress is imposed starting at 10 to 14 days after sowing (DAS) or 7 days after transplanting, and is continued through to silking. Pots are watered by an automated system fitted with timers to provide watering at 25 or 50% of field capacity during the entire period of drought-stress treatment. The intensity and duration of this stress will allow identification of the impact on vegetative growth as well as on the anthesis-silking interval.

Potting mixture: A mixture of ⅓ turface (Profile Products LLC, IL, USA), ⅓ sand and ⅓ SB300 (Sun Gro Horticulture, Wash., USA) can be used. The SB300 can be replaced with Fafard Fine-Germ (Conrad Fafard, Inc., MA, USA) and the proportion of sand in the mixture can be reduced. Thus, a final potting mixture can be ⅜ (37.5%) turface, ⅜ (37.5%) Fafard and ¼ (25%) sand.

Field Capacity Determination: The weight of the soil mixture (w1) to be used in one S200 pot (minus the pot weight) is measured. If all components of the soil mix are not dry, the soil is dried at 100° C. to constant weight before determining w1. The soil in the pot is watered to full saturation and all the gravitational water is allowed to drain out. The weight of the soil (w2) after all gravitational water has seeped out (minus the pot weight) is determined. Field capacity is the weight of the water remaining in the soil obtained as w2−w1. It can be written as a percentage of the oven-dry soil weight.

Stress Treatment: During the early part of plant growth (10 DAS to 21 DAS), the well-watered control has a daily watering of 75% field capacity and the drought-stress treatment has a daily watering of 25% field capacity, both as a single daily dose at or around 10 AM. As the plants grow bigger, by 21 DAS it will become necessary to increase the daily watering of the well-watered control to full field capacity and the drought stress treatment to 50% field capacity.

Nutrient Solution: A modified Hoagland's solution at 1/16 dilution with tap water is used for irrigation.

TABLE 1

Preparation of 20 L of Modified Hoagland's Solution Using the Following Recipe:

| 10X Micronutrient Solution | 16 mL |
|---|---|
| KH2PO4 (MW: 136.02) | 22 g |
| MgSO4 (MW: 120.36) | 77 g |
| KNO3 (MW: 101.2) | 129.5 g |
| Ca(NO3)2•4H2O (MW: 236.15) | 151 g |
| NH4NO3 (MW: 80.04) | 25.6 g |
| Sprint 330 (Iron chelate) | 32 g |

TABLE 2

Preparation of 1 L of 10X Micronutrient Solution Using the Following Recipe:

| 10X Micronutrient Solution | Mg/L |
|---|---|
| H3BO3-30 mM | 1854 |
| MnCl2•4H2O-10 mM | 1980 |
| ZnSO4•7H2O-10 mM | 2874 |
| CuSO4•5H2O-1 mM | 250 |
| H2MoO4•H2O-1 mM | 242 |

Fertilizer grade $KNO_3$ is used.

Automation: Watering can be done using PVC pipes with drilled holes to supply water to systematically positioned pots using a siphoning device. Irrigation scheduling can be done using timers.

Replications: One or more individual plants or samples may be used to evaluate RuBP, PGA or 2-A.

Leaf punches may be started during the stress period at the beginning of visible drought stress symptoms, namely, leaf greying and the start of leaf rolling until the end of the experiment.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. A method for resolving and measuring Ribolose-1,5-biophosphate (RuBP), 3-phosphoglycerate (PGA), and 2-phosphoglycolate (2-PA) in a photosynthetic cellular extract, comprising:
   introducing a photosynthetic cellular extract from a plant into a reverse phase chromatography column; and
   performing reverse phase high performance liquid chromatography on the extract to detect and measure the levels of RuBP, PGA, and 2-PA in said extract.

2. The method of claim 1, further comprising obtaining a photosynthetic cellular extract from a plant.

3. The method of claim 1, further comprising diluting the photosynthetic cellular extract in mobile phase A prior to introduction into the chromatography column.

4. The method of claim 1, further comprising eluting the column with mobile phase B to resolve the RuBP, PGA, and 2-PA.

5. The method of claim 4, wherein the mobile phase A comprises a mixture of water, acetonitrile and formic acid or combinations thereof.

6. The method of claim 5 wherein the mobile phase A comprises 0.04% (v/v) formic acid and 10% (v/v) acetonitrile in water.

7. The method of claim 4, wherein the mobile phase B comprises a mixture of water, acetonitrile and formic acid or combinations thereof.

8. The method of claim 7, wherein the mobile phase B comprises 0.04% (v/v) formic acid and 90% (v/v) acetonitrile in water.

9. The method of claim 3, wherein the mobile phase A comprises an ion pairing reagent.

10. The method of claim 9, wherein the ion pairing reagent is N,N-dimethylhexylamine (0.2% v/v).

11. The method of claim 4, wherein the mobile phase B comprises an ion pairing reagent.

12. The method of claim 11, wherein the ion pairing reagent is N,N-dimethylhexylamine (0.2% v/v).

13. The method of claim 1, wherein performing reverse phase high performance liquid chromatography further comprises a linear gradient comprising holding mobile phase B at about 5% for 0.5 min, then increasing mobile phase B to about 50% in about 1 minute to separate and elute the RuBP, PGA, and 2-PA.

14. The method of claim 1 further comprising detecting and measuring RuBP, PGA, and 2-PA using mass spectrometry.

15. The method of claim 14, wherein mass spectrometry is performed using a tandem mass spectrometer.

16. The method of claim 15, wherein the tandem mass spectrometer is used in the negative ionization mode.

17. The method of claim 15, further comprising detecting RuBP by monitoring daughter ions (m/z 97) of its precursor ions (m/z 309).

18. The method of claim 15, further comprising detecting 2-GA by monitoring daughter ions (m/z 97) of its precursor ions (m/z ratio 185).

19. The method of claim 15, further comprising detecting 2-PA by monitoring daughter ions (m/z 79) of its precursor ion (m/z 155).

20. The method of claim 1, wherein the level of each resolved RuBP, PGA, or 2-PA from a photosynthetic cellular extract is 10 parts per million or more.

21. A method for identifying a plant with increased photosynthetic performance, the method comprising:
   introducing a photosynthetic cellular extract from a first plant and a second plant respectively into a reverse phase chromatography column;
   performing reverse phase high performance liquid chromatography (HPLC) on each extract to resolve RuBP and PGA;
   detecting and measuring the resolved RuBP and PGA using mass spectrometry;
   determining a level of PGA and a ratio of PGA/RuBP in the cellular extract from each plant; and
   comparing the level of PGA and the ratio of PGA/RuBP of the first plant to the level of PGA and the ratio of PGA/RuBP from the second plant, wherein the plant that has a level of PGA and PGA/RuBP ratio that are greater than the level of PGA and PGA/RuBP ratio from the other plant is indicative of a plant with increased photosynthetic performance.

22. The method of claim 21, wherein the first plant is subjected to an abiotic stress selected from the group consisting of drought, cold temperatures, salt, osmotic stress, frost or freeze, high heat temperatures, low light, oxidative stress, chemical stress, or an herbicide.

23. The method of claim 21, wherein the second plant is a control plant.

24. The method of claim 21, further comprising obtaining a photosynthetic cellular extract from a first and a second plant.

25. The method of claim 21, wherein mass spectrometry is performed using a tandem mass spectrometer.

26. The method of claim 21 wherein the tandem mass spectrometer is used in the negative ionization mode.

27. The method of claim 21, further comprising detecting RuBP by monitoring daughter ions (m/z 97) of its precursor ions (m/z 309).

28. The method of claim 21 further comprising detecting PGA by monitoring daughter ions (m/z 97) of its precursor ions (mass/charge ratio 185).

29. The method of claim 21, wherein performing reverse phase high performance liquid chromatography further comprises a linear gradient comprising holding mobile phase B at about 5% for 0.5 min, then increasing mobile phase B to about 50% in about 2 minute to separate and elute the RuBP and PGA.

30. A method for identifying a plant with increased photosynthetic performance, the method comprising:
   introducing a photosynthetic cellular extract from a first plant and a second plant into a reverse phase chromatography column;
   performing reverse phase high performance liquid chromatography on each extract to isolate PGA and 2-PA;
   detecting and measuring the separated PGA and 2-PA using mass spectrometry determining a level of 2-PA and a ratio of 2-PA/PGA in the cellular extract from each plant; and
   comparing the level of 2-PA and the ratio of 2-PA/PGA of the first plant to the level of 2-PA and ratio of 2-PA/PGA from the second plant, wherein the plant that has a level of 2-PA and a 2-PA/PGA ratio that are less than the level of 2-PA and the 2-PA/PGA ratio from the other plant is indicative of a plant with increased photosynthetic performance.

31. The method of claim 30, wherein the first plant is subjected to an abiotic stress selected from the group consisting of drought, cold temperatures, salt, osmotic stress, frost or freeze, high heat temperatures, low light, oxidative stress, and chemical stress or an herbicide.

32. The method of claim 30, further comprising obtaining a photosynthetic cellular extract from a first and a second plant.

33. The method of claim 30, wherein mass spectrometry is performed using a tandem mass spectrometer.

34. The method of claim 33 wherein the tandem mass spectrometer is used in the negative ionization mode.

35. The method of claim 30, wherein the second plant is a control plant.

36. The method of claim 30 further comprising detecting PGA by monitoring daughter ions (m/z 97) of its precursor ions (m/z 185).

37. The method of claim 30 further comprising 2-PA by monitoring daughter ions (m/z 79) of its precursor ion (m/z 155).

38. The method of claim 30, wherein performing reverse phase high performance liquid chromatography further comprises a linear gradient comprising holding mobile phase B at about 5% for 0.5 min, then increasing mobile phase B to about 50% in about 1 minute to separate and elute the PGA and 2-PA.

* * * * *

UNITED STATES PATENT AND TRADEMARK OFFICE
CERTIFICATE OF CORRECTION

PATENT NO.       : 8,110,113 B2
APPLICATION NO.  : 12/110776
DATED            : February 7, 2012
INVENTOR(S)      : Kurek et al.

It is certified that error appears in the above-identified patent and that said Letters Patent is hereby corrected as shown below:

Column 14, Claim 18, line 2, "2-GA" should be --PGA--.

Signed and Sealed this
Tenth Day of April, 2012

David J. Kappos
*Director of the United States Patent and Trademark Office*